(12) United States Patent
Barclay et al.

(10) Patent No.: US 10,067,043 B2
(45) Date of Patent: Sep. 4, 2018

(54) PRESSURE STEPPED MICROWAVE ASSISTED DIGESTION

(71) Applicant: CEM Corporation, Matthews, NC (US)

(72) Inventors: David A. Barclay, College Station, TX (US); Joseph J. Lambert, Charlotte, NC (US); William E. Jennings, Wingate, NC (US); David L. Herman, Charlotte, NC (US)

(73) Assignee: CEM Corporation, Matthews, NC (US)

( * ) Notice: Subject to any disclaimer, the term of this patent is extended or adjusted under 35 U.S.C. 154(b) by 26 days.

(21) Appl. No.: 15/395,002

(22) Filed: Dec. 30, 2016

(65) Prior Publication Data

US 2017/0108415 A1    Apr. 20, 2017

Related U.S. Application Data

(60) Continuation of application No. 13/239,447, filed on Sep. 22, 2011, which is a division of application No.
(Continued)

(51) Int. Cl.
*B01J 19/12*    (2006.01)
*G01N 1/44*    (2006.01)
(Continued)

(52) U.S. Cl.
CPC .............. *G01N 1/44* (2013.01); *B01J 19/126* (2013.01); *H05B 6/6447* (2013.01); *H05B 6/806* (2013.01);
(Continued)

(58) Field of Classification Search
CPC ... G01N 1/44; B01J 19/126; B01J 2219/1215; B01J 2219/0877; B01J 2219/0801;
(Continued)

(56) References Cited

U.S. PATENT DOCUMENTS 2,541,644 A    2/1951    Enabnit
2,828,593 A    4/1958    Colgren et al.
(Continued)

FOREIGN PATENT DOCUMENTS

EP    0198675 B2    4/1994

OTHER PUBLICATIONS

Legere and Salin, "Design and Operation of a Capsule-Based Microwave Digestion System," Analytical Chemistry 998, 70, pp. 5029-5036.

*Primary Examiner* — Nicholas A Smith
*Assistant Examiner* — Colleen M Raphael
(74) *Attorney, Agent, or Firm* — Parsons Summa (57) ABSTRACT

An instrument and method for high pressure microwave assisted chemistry are disclosed. The method includes the steps of applying microwave radiation to a sample in a sealed vessel while measuring the temperature of the sample and measuring the pressure generated inside the vessel and until the measured pressure reaches a designated set point, opening the vessel to release gases until the pressure inside the vessel reaches a lower designated set point, closing the vessel, and repeating the steps of opening the vessel at designated pressure set points and closing the vessel at designated pressure set points to the sample until the sample reaction reaches a designated high temperature. The designated set points can controllably differ from one another as the reaction proceeds. Microwave energy can be applied continuously or intermittently during the opening and closing steps. The apparatus includes a microwave cavity, a microwave transparent pressure resistant reaction vessel in the cavity, a cap on the reaction vessel, a pressure sensor for measuring pressure in the vessel, a temperature sensor, and means for opening and closing the cap at predetermined
(Continued)

pressure set points measured by the pressure sensor to release pressure from the vessel.

10 Claims, 11 Drawing Sheets

Related U.S. Application Data

12/541,262, filed on Aug. 14, 2009, now Pat. No. 9,237,608.

(51) Int. Cl.
*H05B 6/80* (2006.01)
*H05B 6/64* (2006.01)

(52) U.S. Cl.
CPC .. *B01J 2219/0801* (2013.01); *B01J 2219/089* (2013.01); *B01J 2219/0871* (2013.01); *B01J 2219/0877* (2013.01); *B01J 2219/1215* (2013.01); *B01J 2219/1233* (2013.01); *B01J 2219/1275* (2013.01)

(58) Field of Classification Search
CPC .......... B01J 2219/089; B01J 2219/0871; B01J 2219/1275; B01J 2219/1233; H05B 6/806; H05B 6/6447
USPC .................................... 204/157.43
See application file for complete search history.

(56) References Cited

U.S. PATENT DOCUMENTS

| | | |
|---|---|---|
| 3,223,105 A | 12/1965 | Hogel |
| 3,232,092 A | 2/1966 | Glassey |
| 3,300,256 A | 1/1967 | Liebig |
| 3,440,385 A | 4/1969 | Smith |
| 3,791,397 A | 2/1974 | Janu |
| 4,122,964 A | 10/1978 | Morris |
| 4,255,386 A | 3/1981 | Schachter |
| 4,490,597 A | 12/1984 | Mengel |
| 4,616,670 A | 10/1986 | Duffy |
| 4,796,776 A | 1/1989 | Dalquist |
| 4,861,566 A | 8/1989 | Denny |
| 4,877,624 A | 10/1989 | Floyd |
| 4,882,128 A | 11/1989 | Hukvari |
| 4,882,286 A | 11/1989 | Neas |
| 4,923,085 A | 5/1990 | Lillelund |
| 4,946,797 A | 8/1990 | Neas |
| 5,025,335 A | 6/1991 | Stefansky |
| 5,204,065 A | 4/1993 | Floyd |
| 5,215,715 A | 6/1993 | Haswell |
| 5,230,865 A | 7/1993 | Hargett |
| RE34,373 E | 9/1993 | Collins |
| 5,257,549 A | 11/1993 | Mole |
| 5,264,185 A | 11/1993 | Floyd |
| 5,382,414 A | 1/1995 | Lautenschlager |
| 5,420,039 A | 5/1995 | Renoe et al. |
| 5,439,724 A | 8/1995 | Rojek |
| 5,510,153 A | 4/1996 | Lilienthal, II |
| 5,523,053 A | 6/1996 | Dudek |
| 5,531,241 A | 7/1996 | Rasmussen |
| 5,601,745 A | 2/1997 | Schalk |
| 5,620,659 A | 4/1997 | Revesz |
| 5,767,493 A | 6/1998 | Lautenschlager |
| 5,830,417 A | 11/1998 | Kingston |
| 5,948,307 A | 9/1999 | Stalling |
| 6,011,247 A | 1/2000 | Grillo |
| 6,086,826 A | 7/2000 | Thomas |
| 6,097,015 A | 8/2000 | McCullough |
| 6,246,038 B1 | 6/2001 | Thomas |
| 6,286,702 B1 | 9/2001 | Buermann |
| 6,287,526 B1 | 9/2001 | Hargetur |
| 6,575,244 B2 | 6/2003 | Chang |
| 6,602,309 B2 | 8/2003 | Vizulis |
| 6,607,920 B2 | 8/2003 | Jennings |
| 6,744,024 B1 | 6/2004 | Hayes |
| 6,803,237 B2 | 10/2004 | Manganini |
| 6,843,266 B2 | 1/2005 | Hope |
| 6,983,857 B2 | 1/2006 | Miller |
| 6,984,359 B2 | 1/2006 | Florkey |
| 7,144,739 B2 | 12/2006 | Jennings |
| 7,451,692 B2 | 11/2008 | Baraille |
| 7,816,633 B2 | 10/2010 | Hargett, Jr. |
| 2003/0127313 A1 | 7/2003 | Lautenschlager |
| 2004/0004075 A1 | 1/2004 | Morales |
| 2006/0039838 A1 | 2/2006 | Barnhardt |
| 2006/0120914 A1 | 6/2006 | Salda |
| 2007/0045304 A1 | 3/2007 | Liang |
| 2008/0078760 A1 | 4/2008 | Auer |
| 2012/0074136 A1 | 3/2012 | Barclay |
| 2016/0096162 A1 | 4/2016 | Barclay |

PRESSURE STEPPED MICROWAVE ASSISTED DIGESTION

RELATED CASES

This is a continuation of Ser. No. 13/239,447 filed Sep. 22, 2011 for "Pressure Stepped Microwave Assisted Digestion." Ser. No. 13/239,447 is a divisional of Ser. No. 12/541,262 filed Aug. 14, 2009 for "Pressure Stepped Microwave Assisted Digestion."

BACKGROUND

The invention relates to microwave assisted chemical reactions carried out at elevated temperatures and elevated pressures. In this context, the term "digestion" refers to the reaction of a sample with an aggressive acid (e.g., nitric, $HNO_3$) at high temperatures and pressures. The combination of temperature and the strong acid tends to break most, and preferably all, of the chemical bonds in the sample to produce a liquid containing the constituent species, typically elements, of the sample. The liquid can then be analyzed for the presence and amounts of these elements.

Microwave systems are often used to accelerate the digestion process. Microwaves typically interact directly with the digestion acid and sometimes with the sample composition and thus in many cases microwave digestion can be carried out more quickly than digestion using conventional heat sources. Examples include, but are not limited to U.S. Pat. No. 5,420,039, U.S. Pat. No. 4,946,797, and U.S. Pat. No. 4,861,556.

Although digestion can be carried out using several different acids (e.g., sulfuric, nitric, phosphoric, hydrochloric, hydrofluoric, or perchloric), nitric acid offers advantages in some circumstances. In particular, nitric acid avoids forming insoluble compounds with many inorganic samples. Other acids (e.g., sulfuric and hydrochloric) are more likely to form such insoluble compounds during digestion reactions. Thus, nitric acid is often preferred for digestion because it produces a higher quality sample for analytical testing.

In order to digest in $HNO_3$, however, many samples must typically be heated above the atmospheric boiling point of the acid; e.g., nitric acid boils at about 120° C., but many samples do not digest completely unless heated to at least about 200° C., and some samples require temperatures of 250-300° C. Thus, in order to reach higher temperatures, nitric acid digestion must be carried out in a pressurized environment, typically using vessels that can withstand pressures of several hundred pounds per square inch.

In order to prevent catastrophic failure at such pressures, most digestion vessels include some type of release capacity. These include rupture disks or diaphragms that break at a certain pressure (e.g., U.S. Pat. No. 5,230,865). Other digestion vessels will flex to create a small opening, for example between the body of the vessel and its lid, through which the excess pressure can escape (e.g., U.S. Pat. No. 6,287,526). Other systems are described in, for example, U.S. Pat. No. 5,948,307; U.S. Pat. No. 5,204,065; U.S. Pat. No. 5,264,185; U.S. Pat. No. 5,620,659 and EP0198675. These items are exemplary rather than exhaustive or limiting.

Such pressure release systems are effective for their intended purpose, but they lack precise control over the point at which they will release. Additionally, if the vessel re-seals itself, it does so at an arbitrary pressure rather than at a controlled pressure. As another factor, all vessels are ultimately limited in their pressure capacity.

To some extent, the gas-containing capacity of a vessel can be increased by increasing the vessel's size. Larger vessels, however, carry some corresponding disadvantages. They require, of course, larger instruments to accommodate them. From a safety standpoint, the total force within a vessel is a function of the pressure and the area defined by the vessel walls. Thus, larger vessels are subject to larger total forces and carry correspondingly higher risks of catastrophic failure.

Furthermore, in digestion systems where pressure is not released until the reaction is complete (and the vessel and its contents sufficiently cooled), the vessel volume must be sufficient to contain the sample, the acid, and the gases generated by the digestion reaction at the maximum digestion temperature.

Other pressure release systems attempt more sophisticated solutions. Légère and Salin, "Design and Operation of a Capsule-Based Microwave Digestion System," *Analytical Chemistry* 1998, 70, pp. 5029-5036, describe an apparatus and system where a small (8.4 mm diameter, 25 mm length) polymeric gel capsule containing a sample is inserted into a Teflon™ tube. A digestion acid is then added to the tube and the tube is sealed. Microwaves are then applied to the tube, the gel capsule, the acid, and the capsule contents. The capsule breaks and the acid reacts with the sample. On a periodic basis, the application of microwaves is, however, stopped, the tube is proactively cooled with water, and excess gases are released. The technique is limited by the pressure capabilities of the tube and by the temperature at which the capsule material will digest. In other words, because the capsule breaks up and mixes with the digestion acid, the digestion temperatures must be maintained below those temperatures at which the capsule material would digest and add elements to the sample that would produce an improper analysis. According to Légère, polyacrylamide provides an appropriate capsule material, but contains trace quantities of iron, calcium, sodium, aluminum, and magnesium. Furthermore, polyacrylamide will tend to begin digesting at 230° C. As a result, the ongoing digestion reaction of the sample must be maintained sufficiently below 230° C. to avoid any digestion of the capsule and any consequent pollution of the sample results.

The Légère technique appears to have other disadvantages. As one, the reaction returns to atmospheric pressure on a repeated basis, thus effectively cooling the sample and reducing the temperature. As another disadvantage, both the described "flange valve" and the "squeegee" cleaning technique would appear to raise cross-contamination possibilities between and among digestion samples.

SUMMARY

In one aspect, the invention is a method of high pressure microwave assisted chemistry. The method includes the steps of applying microwave radiation to a sample in a sealed vessel while measuring the temperature of the sample and measuring the pressure generated inside the vessel and until the measured pressure reaches a designated set point, opening the vessel to release gases until the measured pressure inside the vessel reaches a lower designated set point (which can be selected rather than arbitrarily accepted), closing the vessel, and repeating the steps of opening the vessel at designated pressure set points and closing the vessel at designated pressure set points until the sample reaction reaches a designated high temperature. The designated set points can controllably differ from one another as the reaction proceeds. Microwave radiation can be applied (or moderated) either continuously or selectively during the overall digestion, and the reaction can be maintained (dwell) at designated temperatures for selected periods of time.

In another aspect, the invention is an apparatus for microwave assisted high pressure high temperature chemistry. In this aspect, the invention includes a microwave cavity, a microwave transparent pressure-resistant reaction vessel in the cavity, a cap on the reaction vessel, a pressure sensor for measuring pressure in the vessel, and means for opening and closing the cap at predetermined pressure set points measured by the pressure sensor to release pressure from the vessel.

In another aspect, the invention is an apparatus for microwave assisted high pressure high temperature chemistry that includes a source of microwave radiation, a microwave cavity in communication with the source, a pressure resistant reaction vessel in the cavity, a flexible cap on the reaction vessel, a cap seal bearing on the flexible cap, a pressure sensor in pressure communication with the flexible cap, a mechanical arrangement for opening and closing the cap seal and the flexible cap at predetermined pressure set points measured by the pressure sensor.

In another aspect, the invention is the combination of a pressure vessel and a venting cap. In this aspect, the invention includes a pressure resistant reaction vessel with a circular mouth at one end thereof and an annular lip extending outwardly from the mouth parallel to the circular plane of the mouth, and a flexible cap on the mouth of the reaction vessel. The flexible cap includes a circular cover over the circular mouth of the vessel, an annular wall surrounding the exterior of the annular lip, an annular ring at the bottom of the annular wall, with the ring projecting underneath the annular lip toward the vessel walls for positioning the flexible cap on the vessel and maintaining the cap in place on the vessel, at least one indentation in the circular cover for minimizing distortion when any contents of the vessel exert pressure against the lid, and at least one opening in the annular wall for providing a ventilation path through the cap when gas pressure in the vessel flexes the cap sufficiently to partially disengage at least a portion of the cap from the vessel.

In another aspect, the invention is a venting cap for pressure vessels for microwave assisted chemistry. The venting cap includes a flexible circular cover for closing the mouth of a reaction vessel, a flexible annular wall depending from the circular cover, a flexible annular ring at the bottom of the annular wall and parallel to the circular cover for positioning the cap on a reaction vessel and maintaining the cap in place on a reaction vessel, at least one indentation in the circular cover for minimizing distortion when any contents of a reaction vessel exert pressure against the cap, and at least one opening in the annular wall for providing a ventilation path through the cap when gas pressure in a reaction vessel flexes the cap sufficiently to partially disengage at least a portion of the cap from the mouth of a reaction vessel.

The foregoing and other objects and advantages of the invention and the manner in which the same are accomplished will become clearer based on the followed detailed description taken in conjunction with the accompanying drawings.

DETAILED DESCRIPTION

The invention is a method of stepwise opening and closing of a digestion vessel at designated pressures to release excess gases (and thus pressure) as a digestion reaction proceeds and as the reaction temperature increases, and without stopping the reaction and (if desired) without stopping the application of microwaves.

Because pressure is vented on a stepwise basis, the overall size of the digestion vessel can be reduced. The digestion vessel can be relatively small because no need exists for the digestion vessel to hold all of the gases generated throughout the entire digestion reaction. Smaller vessels are safer and easier to operate under pressure. The total force exerted within the vessel is a function of the pressure multiplied by the interior area of the vessel. Smaller vessels are thus exposed to a smaller total force. Smaller vessels also cool faster after a reaction is complete, thus reducing overall cycle time.

Periodic stepwise pressure release also prevents the contents of the vessel from generating an aerosol that would possibly carry off some of the elements that are intended to be measured.

Figure 1:
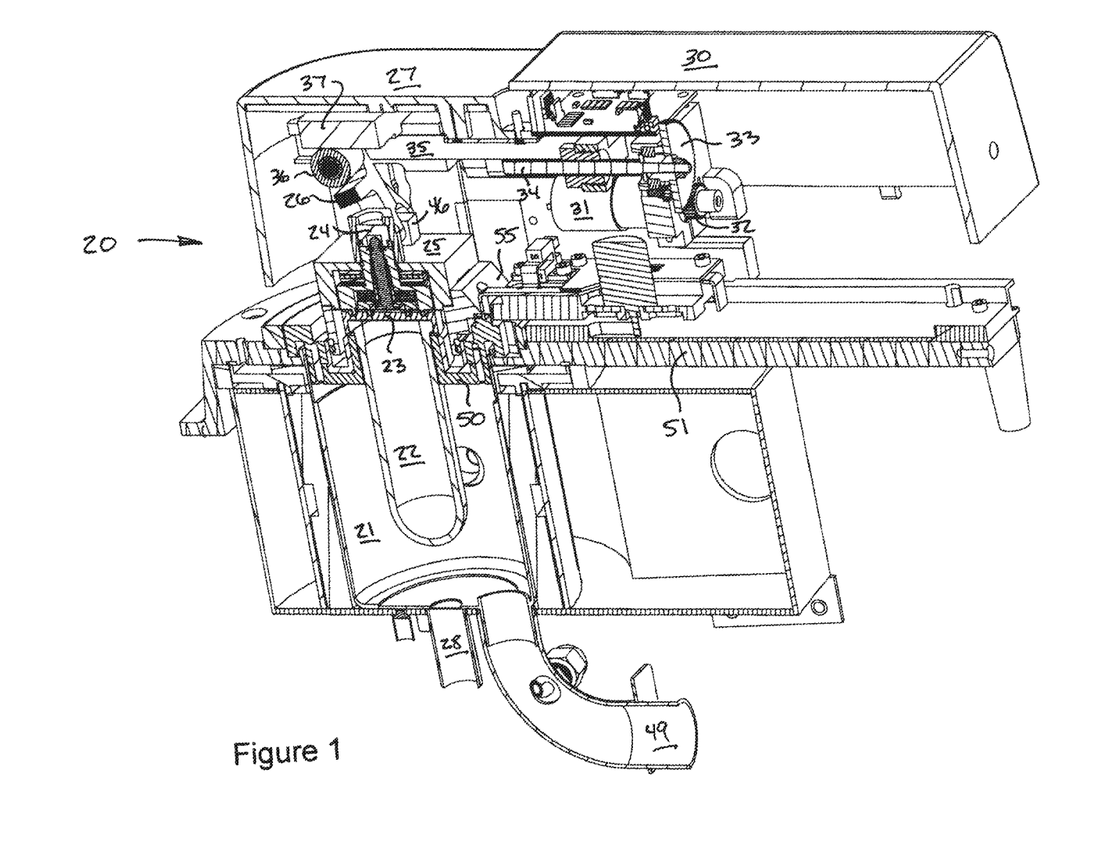
FIG. 1 is a partial cross-sectional perspective view of the interior of an instrument according to the present invention.

FIG. 1 is a partial cross-sectional perspective view of one embodiment of an instrument according to the present invention and broadly designated at 20. In some of its broad aspects, the instrument includes a microwave cavity 21 which in the illustrated embodiment is generally cylindrical in shape. Those familiar with microwave instruments will recognize that a cavity of this type is typically (although not necessarily) cylindrical and cooperates with a microwave source (not shown) to propagate microwaves in the cavity. In exemplary embodiments, and depending upon the nature of the chemical reaction being carried out, the combination of the microwave source and cavity 21 can produce a single mode of microwave radiation in the cavity 21; e.g., commonly assigned U.S. Pat. No. 6,744,024; the contents of which are incorporated entirely herein by reference.

A pressure resistant vessel illustrated as the cylindrical vessel 22 is positioned in the cavity and is closed with a cap (lid) 23. The reaction vessel 22 is transparent to microwave radiation and resistant to chemical attack from strong acids at elevated temperatures. In exemplary embodiments the vessel 22 is formed of a material selected from the group consisting of quartz, composite materials, and polymers. In the digestion context, quartz is often used because it is transparent in the visible frequencies so that the completion of the reaction can be observed or confirmed by an operator. Engineering polymers are appropriate for pressure containment and chemical resistance, but those strong enough to withstand high pressures are typically opaque to visible light.

As used herein, the term "composite materials" refers to combinations of materials that together provide a desired set of properties. For example, engineering polymers are often combined with high strength fibers to produce a structure in which the polymer provides pressure resistance and the fiber provides a flexible matrix that minimizes or eliminates partial or catastrophic failure (typically shattering) of the polymer. As another example, glass (which is typically inappropriate for digestion because it can leach elements) can be coated with PTFE (or another appropriate fluoropolymer) so that the glass portion of the vessel provides the necessary pressure strength while the fluoropolymer coating provides the desired resistance to chemical attack. Appropriate composite materials are well-understood in this art and will not be otherwise described in detail.

In other embodiments a liner can be used inside the vessel so that the vessel provides pressure strength and the liner provides chemical resistance and convenience in use (e.g., when the liner is inexpensive enough to be considered disposable).

The instrument 20 includes means for opening and closing the cap 23 at predetermined pressure set points measured by a pressure sensor illustrated as the load cell 24.

In the illustrated embodiment, a steel block 25 and its associated parts bear against the cap 23 and is connected to an arm 26 that raises and lowers the block 25. These items will be described in more detail with respect to FIGS. 2 and 3.

FIG. 1 illustrates a number of other elements of the instrument. The illustrated embodiment includes a two-part housing with a first portion of the housing 27 being positioned over the cavity and the reaction vessel 22 and a second housing portion 30 being positioned rearward of the cavity and the vessel 22. In operation, and in a manner described with respect to FIGS. 5-7, the instrument includes a motor 31 which, through a drive gear 32 and a driven gear 33, turns a lead screw 34 which is attached to a yoke 35. When the motor 31 moves the lead screw and yoke 35 horizontally, the yoke moves a roller 36 that rests against a roller pad 37.

The roller 36 is in turn connected to the arm 26 which raises and lowers the block 25 to open and close the lid 23 and the vessel 22.

Figure 2:
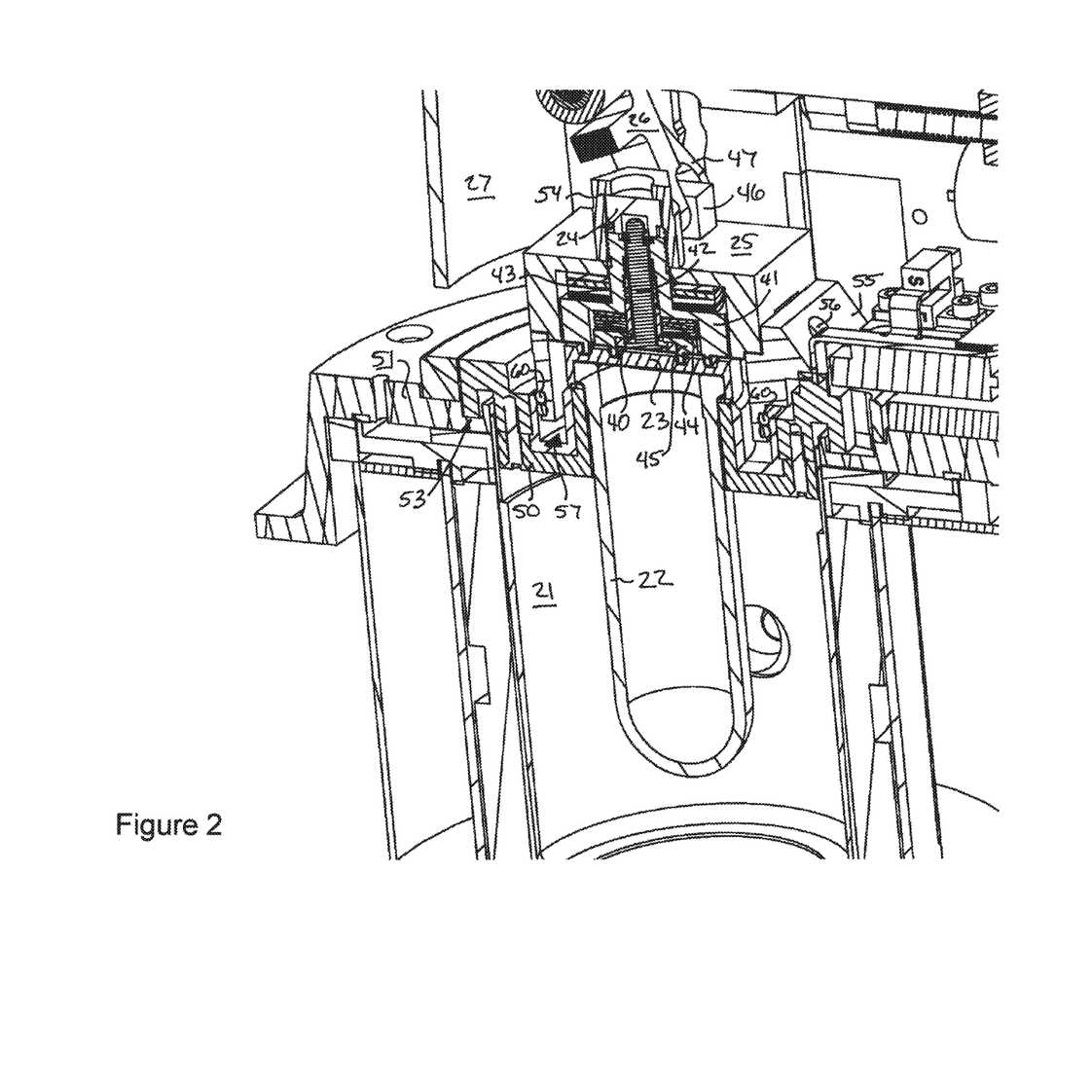
FIG. 2 is a partial cross-sectional perspective view of an enlarged portion of FIG. 1.

FIG. 2 is an enlarged portion of the cross-sectional perspective view of FIG. 1 illustrating the lid 23 and related items in larger detail. Items identical to those in FIG. 1 carry identical reference numerals. Thus, FIG. 2 includes the cavity wall 21, the reaction vessel 22, the lid 23 (the words "lid" and "cap" are used interchangeably in this specification), the steel block 25 and the load cell 24.

FIG. 2 also illustrates that the lid 23 is covered by a diaphragm 40 which is formed of a flexible, chemical-resistant polymer, and which helps protect the sensitive portions of the instrument 20 from contact with potentially corrosive vapors that may be released from the vessel 22.

The steel block 25 holds a lid seal 41 in the shape of an inverted T against the diaphragm 40 and the lid 23. The lid seal 41 surrounds a load transfer rod 42 which bears against the diaphragm 40 and the lid 23 and which is in physical contact with the load cell 24. In this arrangement, pressure generated by the chemical reaction in the vessel 22 exerts a force against the flexible lid 23 which in turn transfers the force through the diaphragm 40 to the load transfer rod 42 and thus to the load cell 24 which provides the desired pressure measurement in signal form. The load cell 24, also referred to as a force transducer or sensor, is a device that translates loads or forces into measurable electrical output. Such load cells are commercially available and well understood by those of ordinary skill in this part.

The cap (lid) 23 is formed of a material that will accurately transfer the pressure inside the vessel to the load transfer rod 42 and to the load cell 24, and that is resistant to chemical attack from strong acids at elevated temperatures. The lid 23 is most often formed of a flexible material, but a rigid cap will work provided that it transfers pressure to the load cell and opens to release pressure when the block 25 is lifted. Silicone polymers (polydimethylsiloxane) are exemplary (but not limiting) materials for the flexible lid 23. Other elastomeric polymers are appropriate provided that they are sufficiently flexible for pressure measurement purposes, can withstand chemical attack during venting, and will not decompose at elevated digestion temperatures. As set forth with respect to FIGS. 8-13, the cap 23 can also include a fluoropolymer liner for direct contact with the digestion components.

A processor (not shown) is in signal communication with the pressure sensor and in communication with the arm 26 and a steel block 25 so that the processor can control the movement of the arm 26 and the block 25 in response to the pressure inside the reaction vessel.

The required programming and processor capacity is well within the capability of a personal computer-type processor, and the use of automated controls and sequences is generally well understood in this and related arts, e.g. Dorf, THE ELECTRICAL ENGINEERING HANDBOOK, 2d Ed. (CRC Press 1997).

FIG. 2 also illustrates that the lid seal 41 is positioned inside the steel block 25 with a first spring 43 bearing against both the block 25 and the lid seal 41 and a second spring 44 bearing against the lid seal 41 and a second lid seal member 45. The springs 43 and 44 exert a fixed downward pressure against the lid 23. Because the lid 23 is maintained under the force of the springs, the lid 23 moves against the load transfer rod 42 only in response to pressure increases within the vessel 22. As a result, the signals from the pressure sensor (load cell) 24 will accurately reflect the pressure in the vessel 22 rather than extraneous movement of the lid or other elements that may be unrelated (or not directly proportional) to the pressure in the vessel 22.

The use of both the first lid seal 41 and the second lid seal 45 provides flexibility in the size of the vessels that the instrument can handle. In the illustrated embodiment, the larger T-shaped lid seal 41 and its associated spring 43 can cover the flexible lid 23 of a larger vessel; typically on the order of 35 milliliters (mL). For smaller samples, the second lid seal member 45 and its associated spring 44 can cover and bear against a smaller lid on a smaller diameter vessel; typically on the order of 10 mL. The use of two separate lid seal members is optional rather than mandatory. The number of different-size diameter vessels that could be incorporated under different lid seals is, of course, conceptually unlimited. In most cases, however, the design will be based on practical considerations and will balance the complexity of the structure against the advantages of its flexibility in operation.

The bottom portion of the load transfer rod 42 is surrounded by a steel ring 48 (FIG. 9) with a square cross-section. The steel ring 48 helps establish a definite area across which the load transfer rod 42 and the load cell 24 measure the pressure. Defining the fixed pressure measurement area using the ring 48 increases the overall accuracy of the pressure measurement step.

The respective springs 43 and 44 also provide a backup against catastrophic failure. Thus, although the instrument and its operation are designed to continually control the pressure using the stepped release of gas from the vessel, if circumstances should arise in which the pressure increases out of control, the springs permit the lid seal 41, or the second lid seal 45, or both to move in response and vent the vessel very rapidly. In such a circumstance, even though control over a single reaction sample might be lost, the pressure release will preserve the instrument for future operation.

FIG. 2 also illustrates that the block 25 includes an ear 46. A clevis 47 is attached to the ear 46 and forms part of the arm 26. This arrangement lifts the block 25 when the arm 26 moves in response to movement of the yoke 35 (FIG. 1). As a result, movement of the clevis 47 on the ear 46 raises and lowers the block 25 and opens and closes the flexible lid 23 on the vessel 22.

FIG. 2 further illustrates that a microwave attenuator 50 forms at least part of the microwave cavity 21. The reaction vessel 22 is supported in the opening defined by the attenuator 50. As FIG. 2 illustrates, the attenuator 50 rests in an annular channel 53 formed in an upper wall 51 adjacent the microwave cavity. This permits the attenuator 50 to be easily removed and replaced which in turn makes it relatively easy to use differently-sized vessels in the cavity and in the attenuator opening. Such a removable attenuator is described in commonly assigned U.S. Pat. No. 6,607,920; the contents of which are incorporated entirely herein by reference.

A retaining bolt 54 helps maintain the load cell 24 in contact with the load transfer rod 42 and the lid seal 41. The interior threads on the retaining bolt 54 correspond to similar threads on the exterior of the upper portion of the lid seal 41.

A vent seal housing 55 is positioned on the attenuator 50 and adjacent the steel block 25. The vent seal housing 55 includes a port 56 that provides gas communication with a channel broadly designated at 57 in the attenuator 50. When pressure is released from the vessel 22 (including through a portion of the lid 23 that is best described with respect to FIGS. 8-13), the escaping gases enter the channel 57 and can be removed through the port 56. For purposes of clarity, the figures illustrate only a portion of the vent seal 55. In actual practice, the vent seal 55 completely surrounds the vessel 22 and the attenuator 50 and includes a second port. Thus, where desired or necessary, a purging or carrier gas can be added to (or removed through) the port 56 (or the second port) and the channel 57. In order to both resist chemical attack and provide shielding to the microwave mode in the cavity, the vent seal 55 is typically formed of a conductive polymer such as polyethylene carrying graphite particles. A pair of O-rings 60 helps provide a seal between the vent seal 55 and the wall of the channel 57.

If desired, the gases that reach the channel 57 can be collected and analyzed. In typical digestion schemes, however, the gases are predictable ($CO_2$, $H_2O$ and various $N_xO_y$ species from the nitric acid) and thus offer little or no information about the sample.

Figure 3:
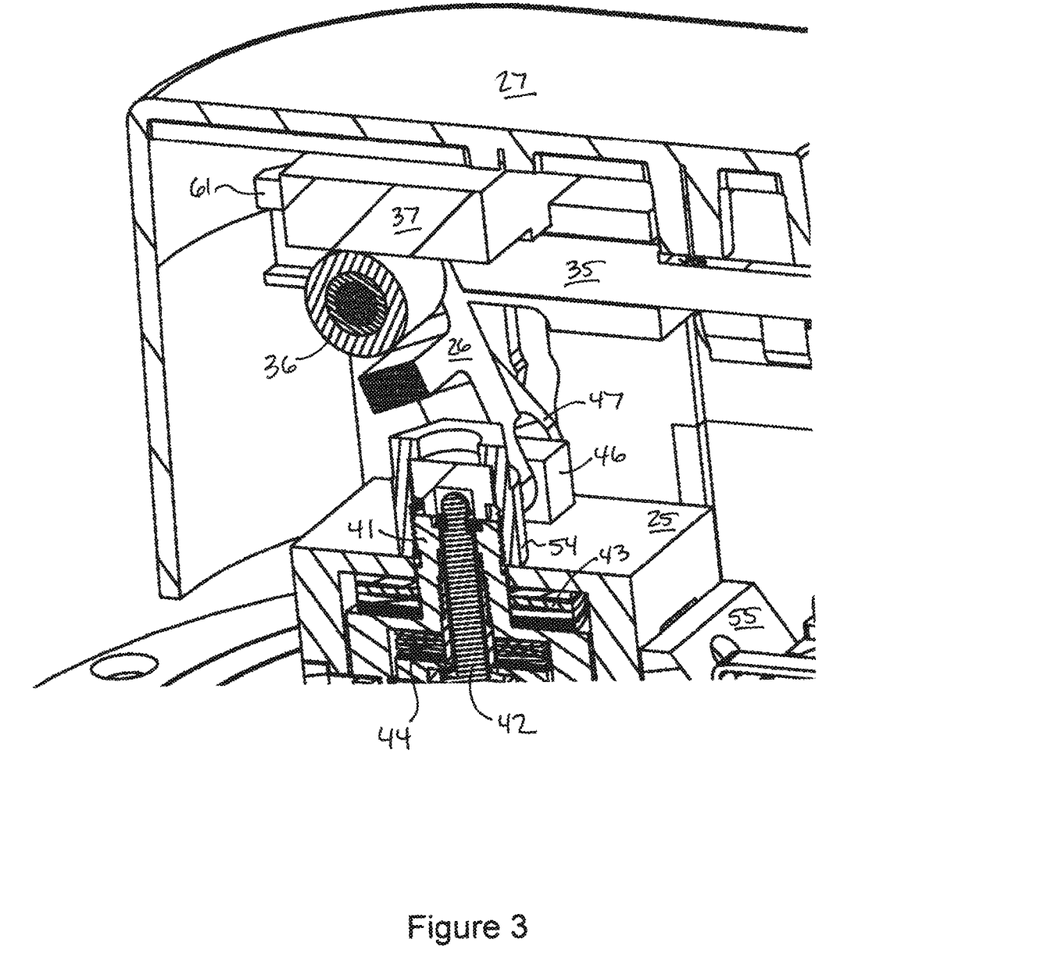
FIG. 3 is another partial cross-sectional perspective view enlarged from a different portion of FIG. 1.

FIG. 3 is another enlarged perspective partial cross-sectional view taken from a portion of FIG. 1 and generally oriented above the view of FIG. 2. FIG. 3 illustrates that the roller 36 moves against the roller pad 37 when the yoke 35 reciprocates horizontally in a yoke holder 61 as the yoke 35 is driven by the lead screw 34. In the orientation of FIGS. 1-3, movement of the roller 36 towards the left represents an opening movement and movement of the roller 36 towards the right indicates a closing movement. This will be described in more detail with respect to FIGS. 5-7.

Figure 4:
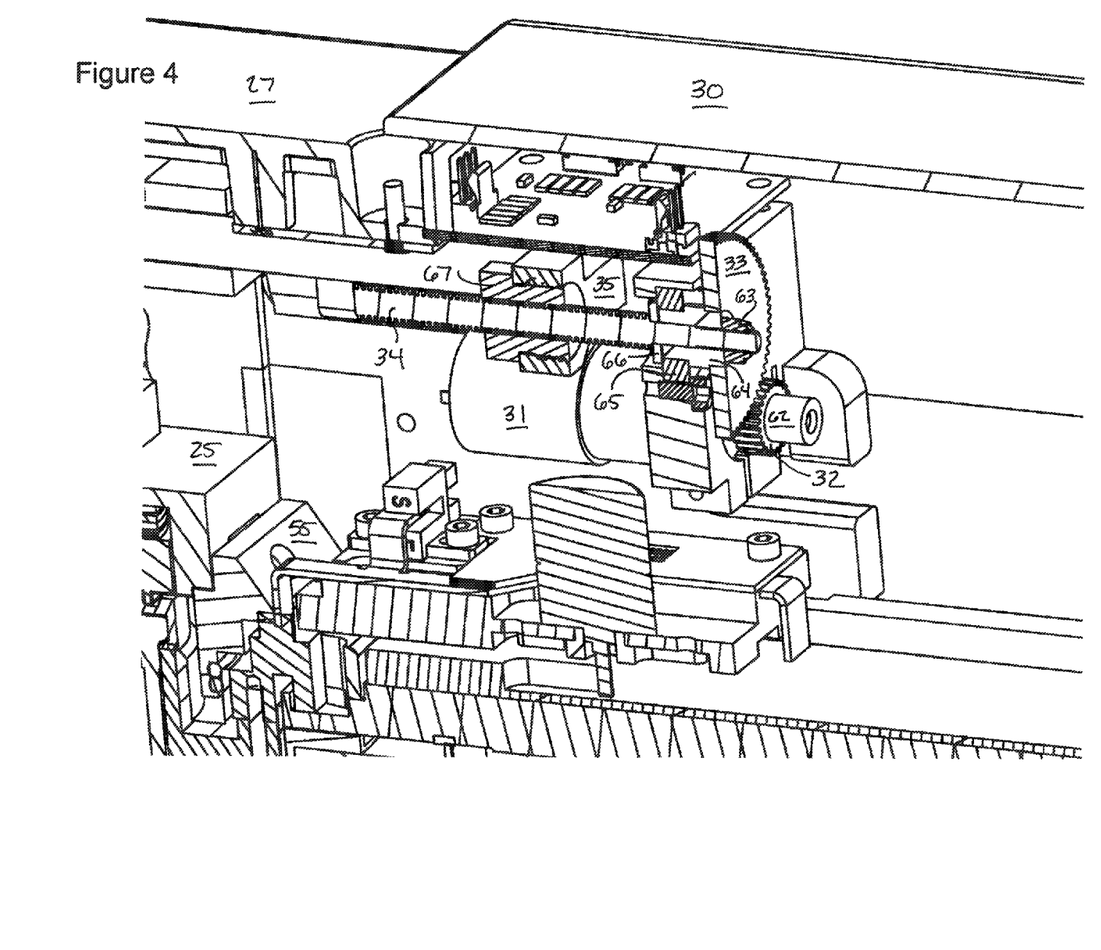
FIG. 4 is a third partial cross-sectional view enlarged from yet another portion of FIG. 1

FIG. 4 is another enlarged partial cross sectional perspective view taken from FIG. 1 and highlights the motor 31 and its associated elements that opens and closes the vessel. The motor 31 is typically an electric motor that turns a shaft 62 which is attached to a drive gear 32. The drive gear 32 propels a driven gear 33 which is fastened to the lead screw 34 with an appropriate nut 63 or equivalent fixture. The driven gear 33 has an annular shaft 64 which turns within a ball or roller bearing 65 which is held in place by a washer 66. The lead screw 34 is moveably attached to the yoke 35 with a second nut 67 so that rotating the lead screw 34 moves the nut 67 and the yoke 35.

Figure 5:
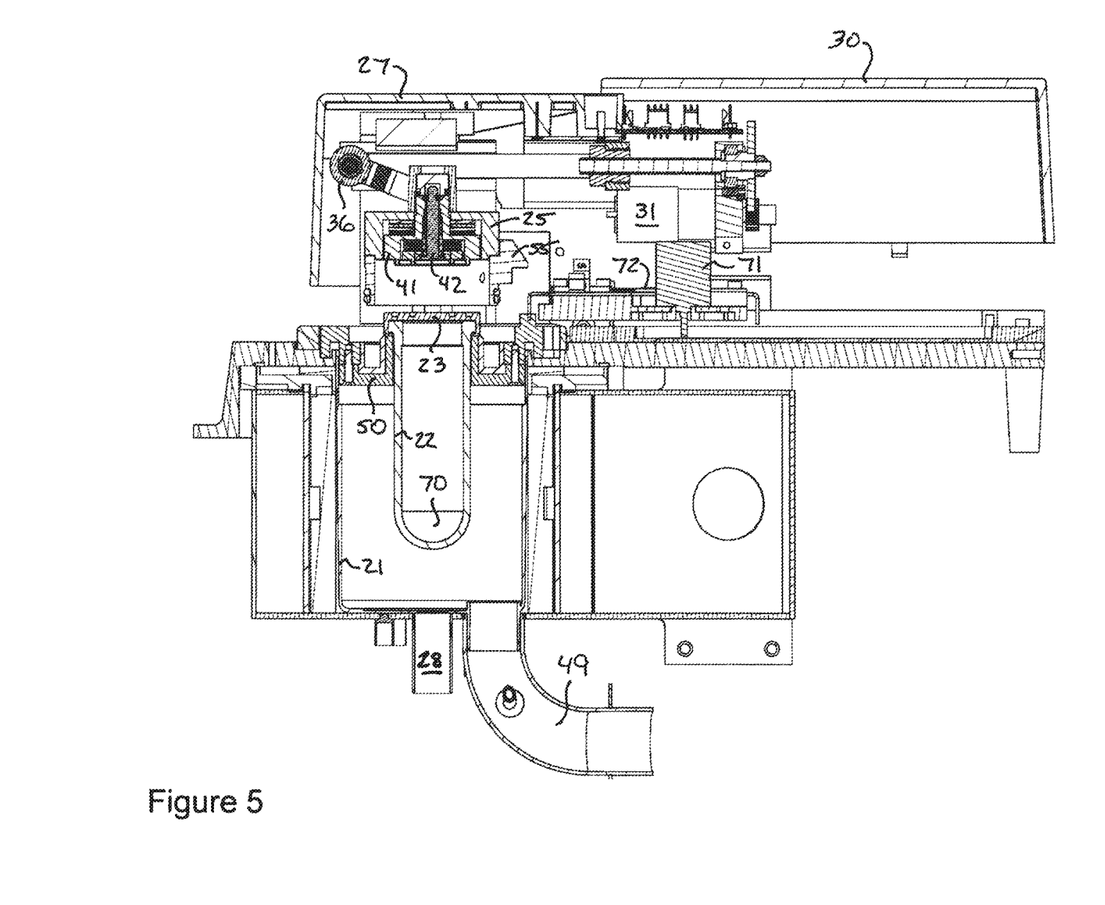
FIG. 5 is a cross-sectional view of an instrument according to the present invention.
Figure 6:
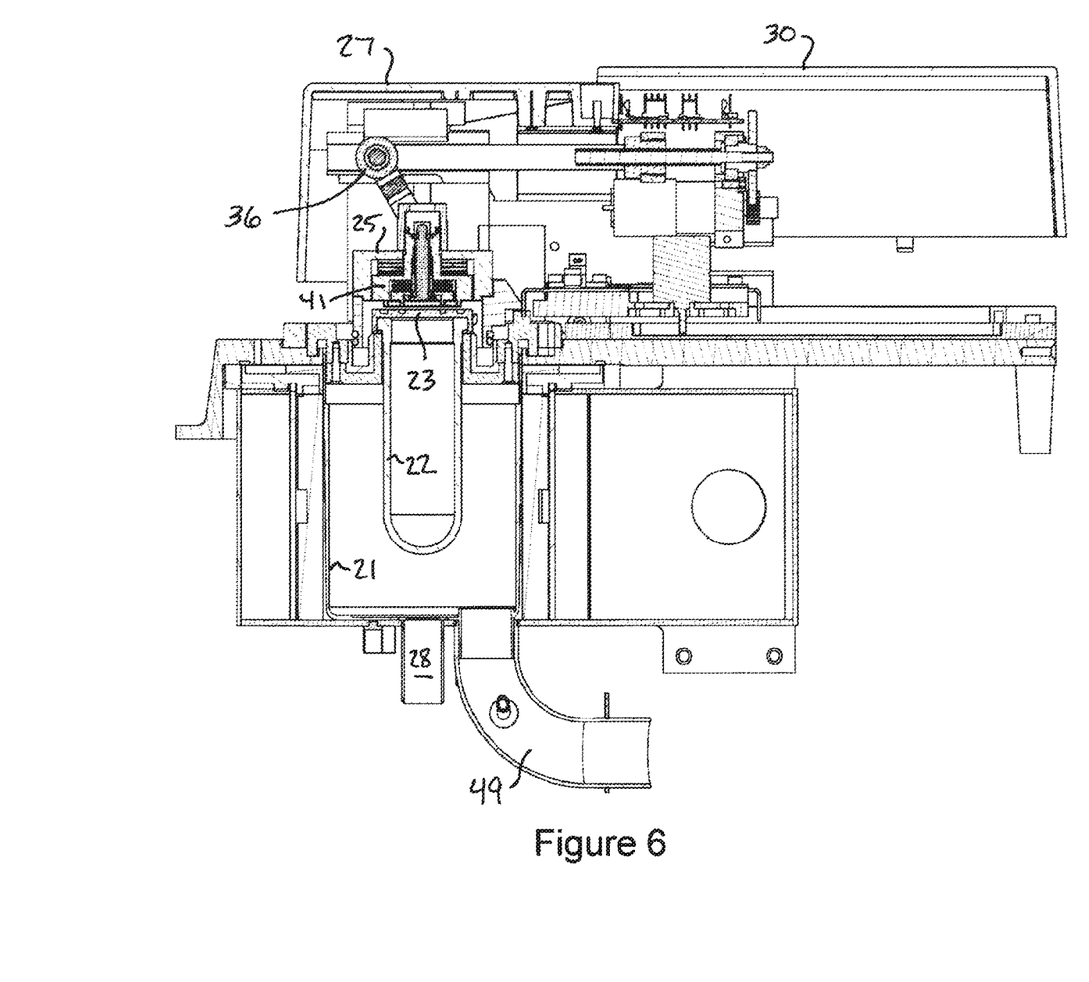
FIGS. 6 and 7 are additional cross-sectional views of the instrument similar to FIG. 5, but illustrating slightly different positional relationships
Figure 7:
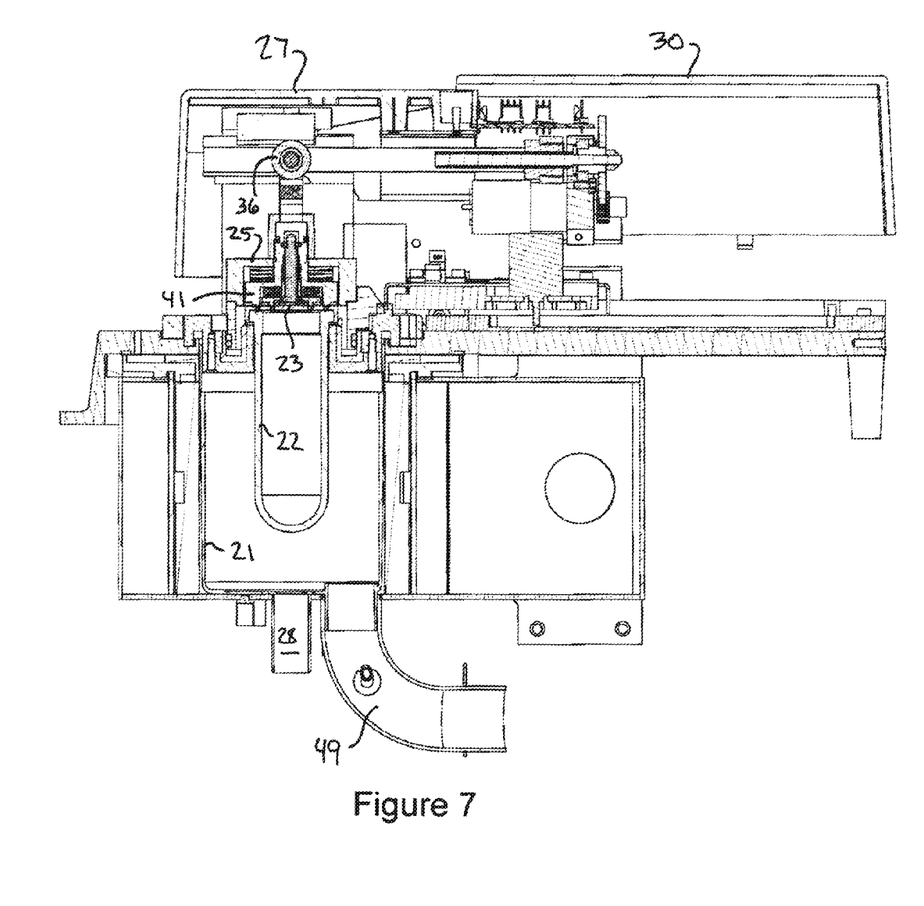

FIGS. 5, 6 and 7 are similar (although not identical) cross sectional views of the instrument 20. The elements illustrated in FIGS. 5, 6 and 7 are identical, but the three figures show the mechanical arrangement that opens and closes the lid 23 in three different positions.

FIG. 5 illustrates the instrument 20 with the steel block 25 and the lid seal 41 in a completely open position. In the open position, the lid seal 41 is raised well above the flexible lid 23 on the vessel 22. FIG. 5 illustrates the vessel 22 in complete cross-section and with a sample 70 schematically indicated at the bottom of the reaction vessel 22.

In the open position of FIG. 5, the roller 36 is in its left-most position with respect to the housing 27, a position in which its relationship with the ear 46 and clevis 47 (not shown in FIG. 5) lift the block 25 and the lid seal 41 into the indicated position.

FIG. 5 also illustrates (in cross-section) a pinion motor 71 immediately beneath the motor 31. The pinion motor 71 drives a rack and pinion that moves the housing 27 and the mechanical opening and closing arrangement laterally as a whole from its position indicated in FIG. 5 to a retracted position (not shown) underneath the second housing portion 30. Portions of the pinion 72 are visible in FIG. 5 and several of the other drawings. When the first housing portion 27 and the associated parts retract into the second housing portion 30, the attenuator 50 is exposed, and the vessel 22 can be easily removed and replaced. The attenuator 50 can likewise be replaced to accommodate a different size vessel 22 or a vessel with a different sized neck.

FIG. 5 also illustrates a vent opening to the cavity, shown as the curved tube 49. A fluid (e.g., air or an inert gas) can be directed through the tube 49 and into the cavity 21 to cool the vessel 22 and the sample 70 in a manner described herein with respect to the method.

FIG. 5 also illustrates an access port 28 into which an appropriate thermal probe (not shown) can be positioned to measure the temperature of the vessel 22 and the sample 70. A non-contact measuring device such as an infrared temperature detector is appropriate for this purpose. Other temperature measuring devices can be used provided they obtain an accurate temperature measurement and do not otherwise interfere with the propagation of microwaves within the cavity 21. The processor is in signal communication with the microwave source and can use the measured temperature or the measured pressure to start, stop or change the propagation of microwave energy into the cavity and thus to the sample.

The remaining elements in FIG. 5 are otherwise the same as those illustrated in FIGS. 1-4.

FIGS. 6 and 7 are otherwise identical to FIG. 5, but show the roller 36 progressively moving to respective partially closed (FIG. 6) and fully closed (FIG. 7) positions. As FIG. 6 indicates, as the roller 36 moves to the right, the steel block 25 and the lid seal 41 move downwardly towards the vessel 22 and the flexible lid 23. As illustrated in FIG. 7, when the roller 36 moves to a position directly above the vessel 22, the arm 26 is completely vertical and the steel block 25 and the lid seal 41 rest directly against the flexible lid 23 thereby sealing the lid 23 against the vessel 22.

It will be understood that although FIGS. 5-7 illustrate the complete opening and closing movement, the invention includes the specific advantage that the instrument can also carry out smaller, incremental opening and closing movements; i.e., to stepwise lower the pressure in the vessel 22 while nevertheless maintaining the pressure above atmospheric pressure.

Figure 8:
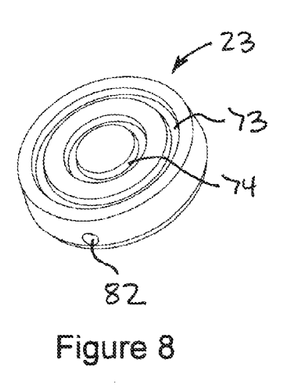
FIG. 8 is a perspective view of a flexible vessel lid according to the invention.
Figure 9:
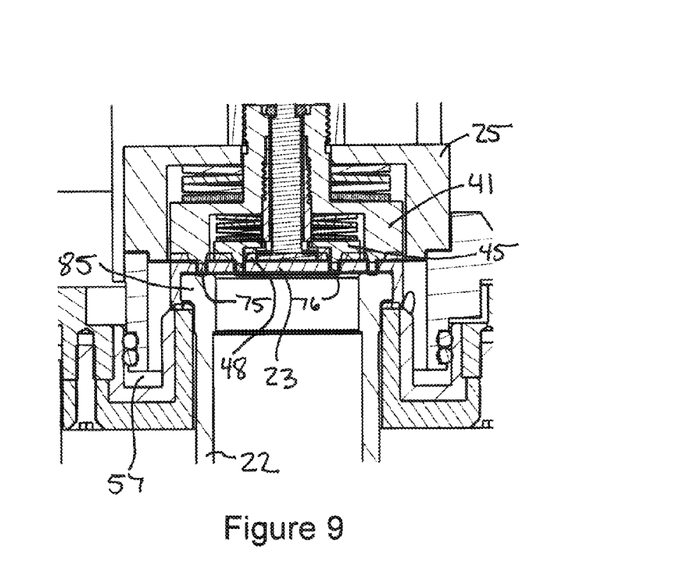
FIG. 9 is a cross-sectional view of the lid of FIG. 8 in its operating environment.

FIGS. 8-13 illustrate aspects of the flexible version of the lid 23. In particular, FIG. 9 is a cross-sectional view showing the lid 23 in context on the vessel 22.

FIG. 8 is a perspective view of the flexible lid 23. The lid 23 includes at least one indentation illustrated in FIG. 8 as the outer annular indentation 73. In this embodiment, the lid 23 also includes a corresponding inner annular indentation 74. As illustrated in FIG. 9, lower portions of the lid seal 41 include one or more depending flanges 75. In particular, FIG. 9 illustrates that the second lid seal member 45 also includes a depending flange 76. In the illustrated embodiment, the depending flanges 75 and 76 are annular and match the (one or more) annular indentations on the lid 23.

The annular indentations 73, 74 and the corresponding flanges 75, 76 help maintain the flexible lid 23, the lid seal 41, the other elements of the mechanical pressure release arrangement in a desired pressure sealing and release relationship with the vessel 22. In particular, when the lid is formed of a material such as a silicone polymer (polydimethylsiloxane) the characteristics of the polymer can encourage it to spread laterally or distort in undesired or unintended directions. Thus, in the orientation of the lid 23 illustrated in FIG. 9, pressure inside the vessel 22 would normally tend to cause the lid 23 to distort both vertically and horizontally (i.e, radially) under pressure. As noted earlier, however, in order to obtain an accurate measurement of the pressure inside the vessel 22, the lid 23 must bear properly against the load transfer rod 42. The relationship between the depending flanges 75, 76 and the annular indentations 73, 74 helps maintain the lid 23 in a proper pressure exerting relationship against the load transfer rod 42 because the flanges minimize or eliminate lateral movement of the lid portions under high pressure in the vessel 22.

The flanges 75, 76 also help increase the efficiency of the seal between the lid 23 and the vessel 22 by exerting the applied downforce over a smaller area (i.e., where a flange meets an indentation).

The indentations are most valuable in the context in which a needle (not shown) is used to pierce the cap; for example to sample a gas or a liquid during the reaction. In other circumstances, and particularly if the lid 23 is not pierced, the indentations can be omitted.

Figure 10:
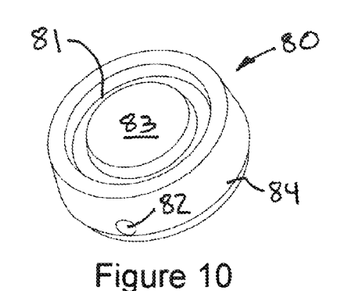
FIG. 10 is a perspective view of a second embodiment of a flexible vessel lid according to the invention.

FIGS. 10-13 illustrate another embodiment of the lid broadly designated at 80. The illustrated lid 80 is substantially identical to the illustrated lid 23 with the only difference being that the lid 80 includes only one annular indentation 81. Some of the other features of the lid are thus more clearly illustrated with respect to the lid 80. For example, both FIGS. 8 and 10 illustrate a vent opening 82 in the respective lids 23 and 80.

As illustrated in FIG. 10, the lid 80 includes a circular cover 83 which in use (e.g., FIG. 9) is positioned over the circular mouth of the vessel 22. An annular wall 84 surrounds the exterior of an annular lip 85 (FIG. 9) which is a typical and useful feature of exemplary reaction vessels such as the illustrated vessel 22. The lid 80 further includes an annular ring 86 (FIG. 12) at the bottom of the annular wall 84 with the ring 86 projecting underneath the annular lip 85 of the vessel 22 and toward the wall of the vessel 22 for positioning the lid 23, 80 on the vessel 22 and maintaining the lid 23, 80 in place on the vessel.

The well 84 and the ring 86 help maintain the cap 23 in place on the vessel 22, form a seal with the attenuator 50, and cushions the lip of the vessel 22 where it meets the attenuator 50.

Figure 11:
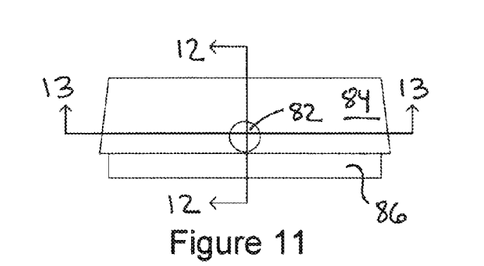
FIG. 11 is a side elevation view of the lid of FIG. 10.
Figure 12:
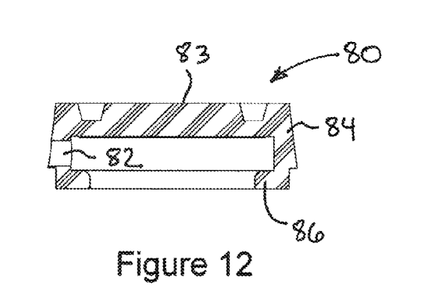
FIG. 12 is a cross-sectional view taken along lines 12-12 of FIG. 11.
Figure 13:
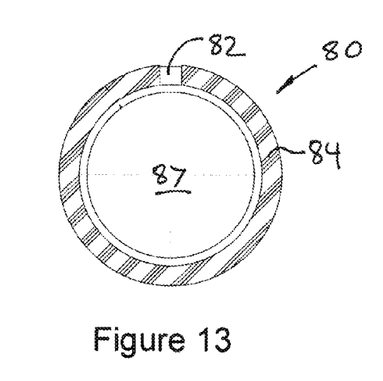
FIG. 13 is a cross-sectional view taken along lines 13-13 of FIG. 11.

FIG. 11 is a side elevation view of the lid 80 illustrating the annular wall 84 and the vent opening 82. FIG. 12 is a cross sectional view taken along lines 12-12 of FIG. 11 and illustrates that the vent opening 82 extends entirely through the annular wall 84 of the lid 23, 80. FIG. 13 is a cross-sectional view taken along the lines 13-13 of FIG. 11 and likewise illustrates the position of the vent opening 82. FIG. 13 also illustrates that if desired, a portion 87 of a more chemically robust material such as a fluorocarbon polymer (e.g., PTFE) can form the interior of the lid 23, 80. Alternatively, the fluorocarbon can be included as a separate piece; i.e., a circular disc. As recognized by those familiar with these materials, the silicone polymers are chemically quite robust, but the fluorocarbon polymers are in many cases the most robust available for resisting attack from harsh chemicals such as the acids used in the high temperature digestion context of the present invention.

Accordingly, under pressure, when the mechanical arrangement is used to slightly lift the lid seal 41, gas pressure can and will distort the lid 23, 80 in a correspondingly slight manner to allow gases to escape through the opening 82 into the venting channel 57 described with respect to FIG. 2 and illustrated in cross-section in FIG. 9.

The flexible lid 23 provides advantages over certain valve-type systems (e.g., Légère, supra). Using the invention, an individual lid can be maintained with a single vessel. Thus, when a new sample is digested, the reaction can be carried out in a fresh (clean) vessel with a fresh cap, thus entirely avoiding the cross-contamination potential that exists when a common valve or vessel are exposed to many different samples.

In another aspect, the invention is a method of high pressure microwave assisted chemistry. In this aspect, the invention includes the steps of applying microwave radiation to a sample in a sealed vessel while measuring the temperature of the sample and measuring the pressure generated inside the vessel and until the measured pressure reaches a designated set point above atmospheric pressure. The vessel is then opened to release gases until the measured pressure inside the vessel reaches a lower designated set point above atmospheric pressure; i.e., a pressure lower than the initial designated set point. The vessel is then closed at the lower designated pressure set point. These steps—opening the vessel at designated pressure set points and then closing the vessel at other designated set points—are repeated until the sample reaches a designated high temperature.

The microwave radiation can be applied continuously during the venting (open and closing) steps or in time-limited or power-limited intervals as may be desired or necessary.

As set forth with respect to the instrument, the invention is particularly useful for carrying out digestion reactions using concentrated nitric acid. The microwave radiation is initially applied until the pressure reaches a designated set point above atmospheric pressure.

As set forth with respect to the instrument, in some circumstances it is helpful or necessary to apply a single mode of microwave radiation to the sample and as those familiar with the propagation of microwaves are well aware, a single mode can be propagated by properly matching a source (i.e., frequency or impedance or both) to the cavity shape and size and tuning (if necessary) the cavity appropriately. Microwave sources suitable for digestion reactions are widely available and well-understood in this art. Magnetrons, klystrons and solid state devices are all appropriate in the digestion context.

Where advantageous, the steps of opening and closing the vessel can be carried out at temperatures above the atmospheric boiling point of the acid. For digestion reactions, temperatures sufficient to break down the chemical bonds of the sample will be required. If this temperature is higher than the atmospheric boiling point of the acid, the sample will fail to digest unless the pressure can be increased sufficiently to raise the boiling point of the acid.

In the method, the vessel can be closed while the pressure continues to remain above atmospheric pressure; i.e., the method does not require an equilibrium between the ambient pressure and the pressure inside the vessel nor does it require the contents of the vessel to reach atmospheric pressure during the venting steps. Instead, the method can selectively reduce the pressure sufficiently to prevent pressure-related failure of the vessel or the instrument while nevertheless continuing to carry out the reaction at or above atmospheric pressure.

Furthermore, the set points need not be identical as the reaction proceeds; a feature that is unavailable using static devices such as springs, frames or diaphragms. Instead (and as set forth in the Examples herein), different set points can be programmed for different pressures, time intervals, or temperatures as the reaction proceeds.

The method can also include the step of measuring the temperature of the vessel and the sample during any of the microwave-applying, vessel-opening and vessel-closing steps. In turn, the method can include moderating the application of microwave energy (typically on a time-limited or power-limited basis) in response to the measured temperature. As used herein, the phrase, "moderating the application of microwave energy," can include initiating, changing, or stopping the application of microwaves.

The method can further comprise thermally managing the reaction temperature, with an exemplary method including the step of proactively cooling the reaction vessel, usually by directing a fluid into contact with the vessel, during any one or more of the steps of applying microwave radiation, opening the vessel, or closing the vessel.

In the method of the invention, the microwave radiation is applied (and if desired, moderated) based on the measured temperature. The venting steps are carried out based upon the measured pressure and thus can be independent of the application of microwave energy and independent of the measured temperature.

Examples

Figure 14:
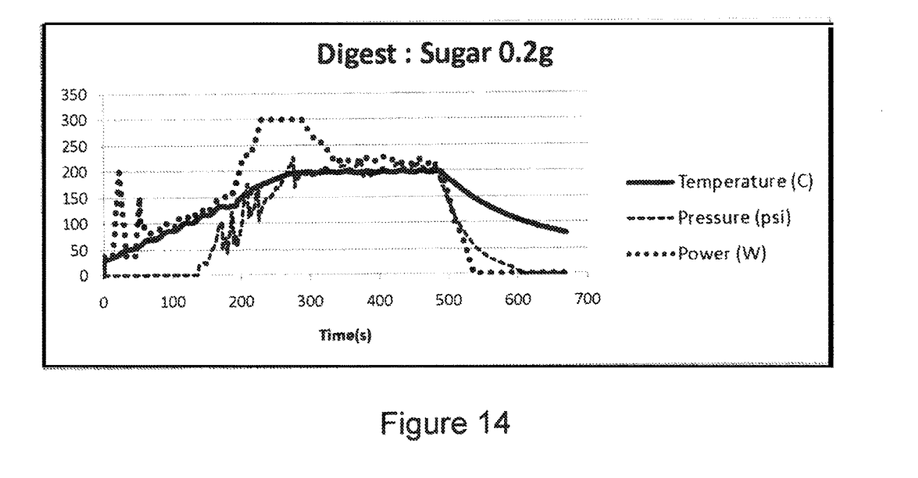
FIGS. 14, 15 and 16 are combined plots of temperature, pressure and applied microwave power for respective digestions carried out on samples of sugar, oil, and tea.

FIGS. 14-19 illustrate the progression of pressure, temperature and microwave power during exemplary digestion reactions. FIG. 14 plots the digestion of a sugar sample, FIG. 15 an oil sample, and FIG. 16 a tea leaf sample. These are exemplary of different types of materials analyzed using digestion. Sugar, being an organic molecule, will tend to generate a relatively large volume of gas. Oil is a hydrocarbon liquid that requires robust conditions before breaking down. Tea leaves represent vegetable organic material.

For each of these examples, the indicated amount of sample was combined with 10 mL of concentrated (68%) nitric acid. The instrument was set (programmed) to generate a five minute ramp from the starting temperature (e.g, 25° C.) to 200° C. followed by a three minute hold at 200° C. Based on the feedback controls in the instrument, the instrument automatically adjusts the power to follow this temperature protocol.

Independently of the temperature, the instrument was programmed to vent in the following manner:

The sugar sample was programmed for two vent openings at 100 pounds per square inch (psi), two at 160 psi, two at 220 psi, two at 250 psi and then as many as necessary at 280 psi.

For the tea (FIG. 16) and the oil (FIG. 15), the venting was programmed for two openings at 200 psi, two at 260 psi, two at 280 psi, and as many as necessary at 300 psi.

Figure 15:
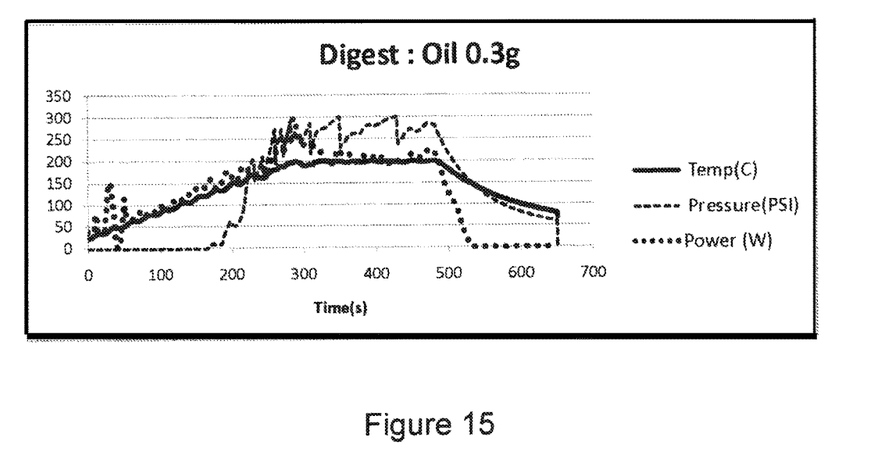

The reaction, of course, does not necessarily reach all of the programmed pressure points. Thus, FIG. 15 illustrates that the oil sample reached 300 psi and was vented (to 250 psi) whenever it reached 300 psi. The sugar sample (FIG. 14) reached a maximum pressure of about 225 psi, and the tea sample (FIG. 16) reached a maximum of about 275 psi.

In each of the vent steps for each of the samples, the vessel was opened at a pressure above atmospheric pressure and then closed at a lower pressure, but one that remained above atmospheric pressure. Thus, when the sugar was vented at 100 psi, the vessel was closed when the pressure dropped to 50 psi. Likewise, when the pressure reached 160 psi, venting was carried out until the pressure drop to 100 psi and when the pressure exceeded 220 psi, venting was carried out until the pressure dropped to approximately 175 psi. Similar protocols were followed for the samples illustrated in FIGS. 15 and 16 and the pressure plots demonstrate this.

Figure 16:
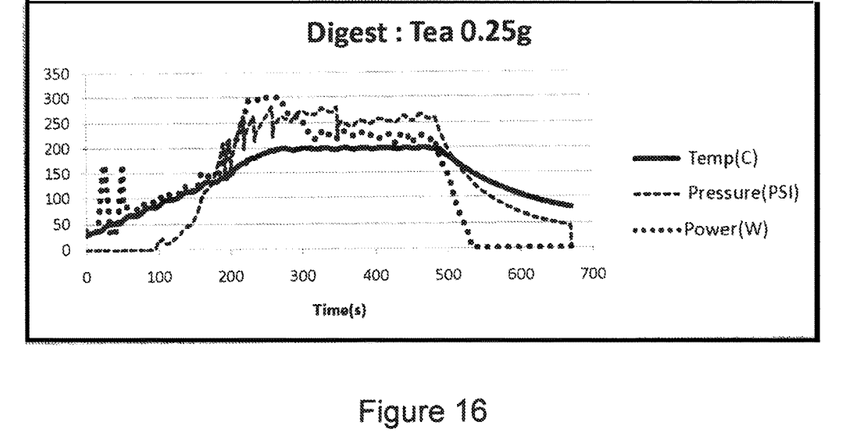
Figure 17:
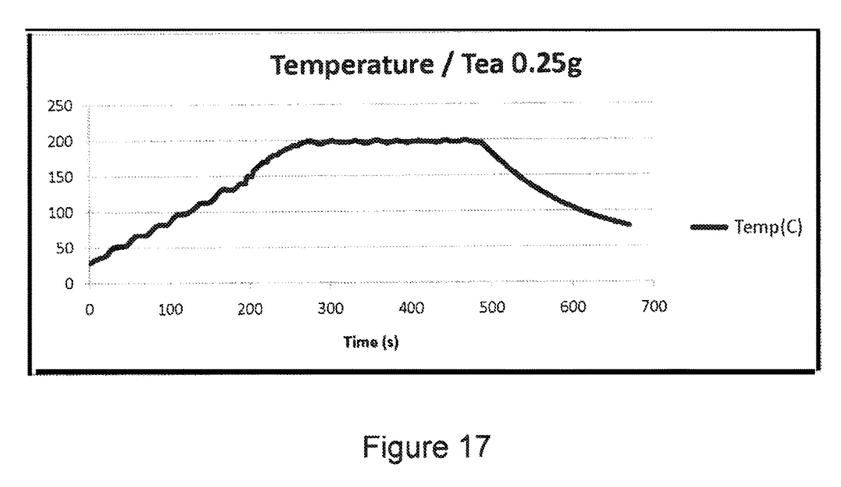
FIGS. 17, 18 and 19 are separate breakout versions of the plots illustrated in FIG. 16.
Figure 18:
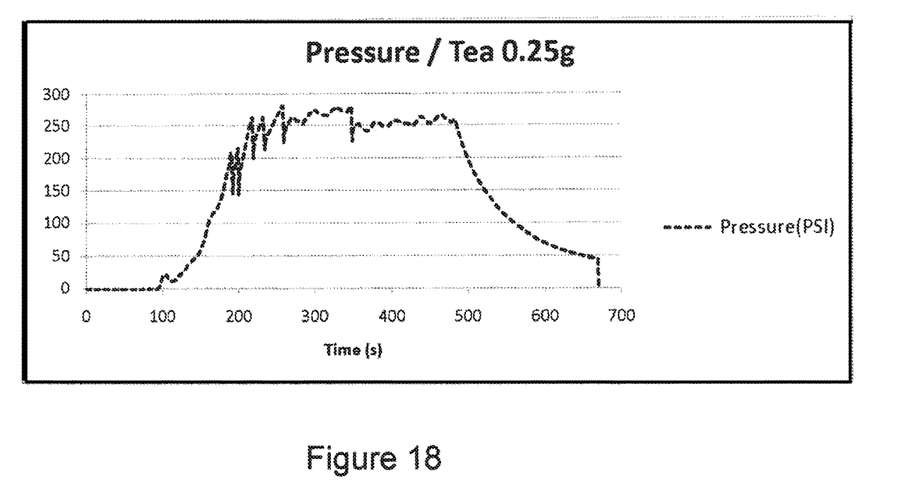
Figure 19:
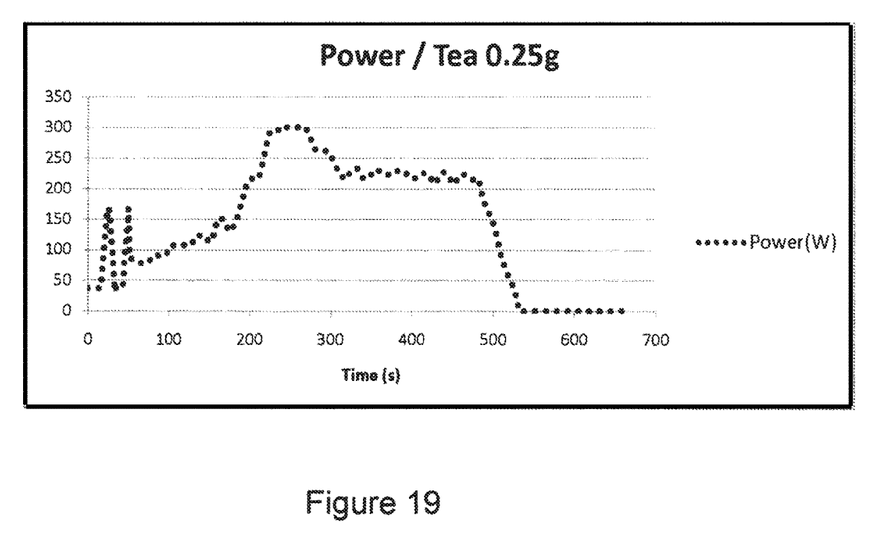

As each of FIGS. 14, 15 and 16 indicate, as microwave power is applied, the temperature and pressure both increase. The pressure increases, however, are accompanied by the specific release steps of the method of the invention. When illustrated in FIGS. 14-16, the pressure release steps appear as the jagged up-and-down entries in the respective dashed lines. The temperature (solid line) tends to increase more smoothly based on the manner in which the instrument is programmed and then can be maintained at a desired set point (200° C. for these samples) until the reaction is complete. When the reaction is completed, the sample is allowed to cool. As set forth earlier, the microwave power (dotted line) is adjusted based on the difference between the measured temperature and the desired (programmed) temperature. The venting can take place independently of the temperature based on the measured pressure.

In the drawings and specification there has been set forth a preferred embodiment of the invention, and although specific terms have been employed, they are used in a generic and descriptive sense only and not for purposes of limitation, the scope of the invention being defined in the claims.

The invention claimed is:

1. A method of high pressure microwave assisted chemistry comprising:
    exerting a defined downward pressure against a flexible lid that seals a microwave-transparent vessel with a sample and at least one acid inside the vessel, with the acid being selected from the group consisting of sulfuric, nitric, phosphoric, hydrochloric, hydrofluoric, perchloric and mixtures thereof;
    applying microwave radiation to the sample and the acid in the sealed vessel to heat the sample and the acid while measuring the temperature of the sample and the acid;
    measuring the pressure generated inside the vessel and until the measured pressure reaches a designated set point above atmospheric pressure;
    releasing gases from the vessel through the flexible lid when the measured pressure inside the vessel exceeds the defined downward pressure and reaches a lower designated set point that remains above atmospheric pressure;
    closing the vessel while the pressure inside the vessel remains above atmospheric pressure; and;
    repeating the steps of opening the vessel at designated pressure set points and closing the vessel at designated pressure set points, and applying microwave radiation to the sample and the acid inside the vessel until the sample reaction inside the vessel reaches a designated temperature.

2. A method according to claim 1 comprising applying microwave radiation during any of the opening or closing steps.

3. A method according to claim 1 comprising applying the microwave radiation until the pressure reaches a designated set point above atmospheric pressure.

4. A method according to claim 1 wherein the step of repeating the opening of the vessel comprises opening the vessel at two designated measured pressure set points that are different pressures from one another.

5. A method according to claim 1 comprising applying a single mode of microwave radiation to the sample.

6. A method according to claim 1 comprising opening the vessel at a temperature above the atmospheric boiling point of the acid.

7. A method according to claim 6 comprising moderating the application of microwave energy in response to the measured temperature.

8. A method according to claim 1 further comprising thermally managing the sample temperature.

9. A method according to claim 1 comprising proactively cooling the reaction vessel during any one or more of the steps of applying microwave radiation, releasing gases from the vessel, and closing the vessel.

10. A method according to claim 9 comprising cooling the vessel by directing a fluid into contact with the vessel.

* * * * *